(12) United States Patent
Yuen et al.

(10) Patent No.: US 7,605,135 B2
(45) Date of Patent: Oct. 20, 2009

(54) BAICALIN AS A TREATMENT FOR SARS INFECTION

(75) Inventors: Kwok Yung Yuen, Hong Kong (CN); Feng Chen, Hong Kong (CN); Kwok Hung Chan, Hong Kong (CN); Yi Tsun Kao, Hong Kong (CN); Yi Guan, Hong Kong (CN); Leo Lit Man Poon, Hong Kong (CN); JSM Peiris, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 869 days.

(21) Appl. No.: 10/983,985

(22) Filed: Nov. 8, 2004

(65) Prior Publication Data

US 2005/0215494 A1      Sep. 29, 2005

Related U.S. Application Data

(60) Provisional application No. 60/518,998, filed on Nov. 10, 2003.

(51) Int. Cl.
*A01N 43/04* (2006.01)
(52) U.S. Cl. ........................................ 514/33
(58) Field of Classification Search ............. 514/33
See application file for complete search history.

(56) References Cited

U.S. PATENT DOCUMENTS 5,106,619 A * 4/1992 Wiesehahn et al. ...... 424/208.1
5,411,733 A * 5/1995 Hozumi et al. ............. 424/727

FOREIGN PATENT DOCUMENTS

WO      WO93/23421 A * 11/1993
WO      WO99/34812   * 7/1999

* cited by examiner

*Primary Examiner*—San-ming Hui
(74) *Attorney, Agent, or Firm*—Saliwanchik, Lloyd & Saliwanchik

(57) ABSTRACT

The present invention relates to a pharmaceutical composition useful for the treatment of diseases associated with viruses of the order Nidovirales of the family Coronaviradae, such as Severe Acute Respiratory Syndrome (SARS) viruses in humans and other animals. In particular, this invention relates to a naturally occurring compound, namely, baicalin, extracted and purified from the Chinese medicinal plant *Scutellaria baicalensis* Georgi (Chinese name: Huang Qin), that exhibits potent antiviral activity against members of the order Nidovirales of the family Coronaviradae that infects humans and other animals; in particular, SARS viruses in humans ("hSARS virus"). The invention also relates to a therapeutic method, using pharmaceutical compositions comprising baicalin compounds, for the treatment, amelioration, management or prevention of diseases associated with members of the order Nidovirales of the family Coronaviradae, such as hSARS.

10 Claims, 4 Drawing Sheets

BAICALIN AS A TREATMENT FOR SARS INFECTION

This application claims priority benefit to U.S. provisional application No. 60/518,998, filed Nov. 10, 2003, which is incorporated herein by reference in its entirety.

1. FIELD OF THE INVENTION

The present invention relates to therapeutic agents useful for the treatment of diseases associated with the order Nidovirales of the family Coronaviradae, such as Severe Acute Respiratory Syndrome (SARS) in humans and other animals. The therapeutic agents of the present invention relate to highly purified forms of traditional Chinese medicines. In particular, this invention relates to a naturally occurring compound, namely, baicalin, extracted and purified from the Chinese medicinal plant *Scutellaria baicalensis* Georgi (Chinese name: Huang Qin), that exhibits potent antiviral activity against members of the order Nidovirales of the family Coronaviradae that infects humans and other animals; in particular, the virus causing Severe Acute Respiratory Syndrome (SARS) in humans ("hSARS virus"). Baicalin is known to be less toxic than many currently available antiviral agents. Baicalin and its derivatives thus represent a novel class of compounds with potential for the development of safe drugs for therapy of infections caused by members of Coronaviradae such as the hSARS virus, and other related infections. The invention also relates to a therapeutic method, using therapeutics comprising baicalin compounds, for the treatment, amelioration, management or prevention of diseases associated with members of the order Nidovirales of the family Coronaviradae that infect at least humans; in particular, the members of Coronaviradae that are strains of the hSARS virus.

2. BACKGROUND OF THE INVENTION

Recently, there has been an outbreak of a typical pneumonia in Guangdong province in mainland China. Between November 2002 and March 2003, there were 792 reported cases with 31 fatalities (WHO. Severe Acute Respiratory Syndrome (SARS) Weekly Epidemiol. Rec. 2003; 78: 86). In response to this crisis, the Hospital Authority in Hong Kong has increased the surveillance on patients with severe a typical pneumonia. In the course of this investigation, a number of clusters of health care workers with the disease were identified. In addition, there were clusters of pneumonia incidents among persons in close contact with those infected. The disease was unusual in its severity and its progression in spite of the antibiotic treatment typical for the bacterial pathogens that are known to be commonly associated with a typical pneumonia.

The first SARS pandemic of the new millennium has affected 8,422 people with 916 fatalities [World Health Organization, Summary table of SARS by country, Nov. 1, 2002 to Aug. 7, 2003. Available at: http://www.who.int/csr/sars/country/en/country2003_08_15.pdf. Accessed Sep. 30, 2003]. A new hSARS virus was consistently isolated from those patients who seroconverted specifically to the virus and confirmed to reproduce SARS in a primate model [Fouchier R A et al., "Aetiology: Koch's Postulates fulfilled for SARS virus." *Nature* 2003; 423:240; Kuiken T et al., "Newly discovered coronavirus as the primary cause of severe acute respiratory syndrome." *Lancet* 2003; 362:263-70]. Though the pandemic has been successfully contained with quarantine and infection control measures, the presence of this virus in wild game food animals [Guan Y et al., "Isolation and characterization of viruses related to the SARS coronavirus from animals in Southern China." *Science* 2003; 302:276-78] and possible seasonality of this disease suggest that recurrence of such an epidemic is likely. Since all age sectors are affected and a high fatality is noted in the elderly and those with co-morbidities [Donnelly C A et al., "Epidemiological determinants of spread of causal agent of severe acute respiratory syndrome in Hong Kong." *Lancet* 2003; 361:1767-72], there is an urgent need to find a cure.

Prospective clinical and viral load studies in nasopharyngeal secretions from SARS patients showed that viral replication peaked at the tenth day after the onset of symptoms [Peiris J S et al., "Clinical progression and viral load in a community outbreak of coronavirus-associated SARS pneumonia: a prospective study." *Lancet* 2003; 361:1767-72]. This viral replicative phase is followed by an immune control phase with decrease of viral load and concomitant appearance of specific neutralizing antibody. However, about one third of the patients continued to go into respiratory failure due to diffuse alveolar damage during this immune control phase, which suggests that part of the damage is related to immunodysregulation [Nicholls J M et al., "Lung pathology of fatal severe acute respiratory syndrome." *Lancet* 2003; 361:1773-8].

At the moment, there are no commercially available antiviral agents which are tailor-made for the hSARS viruses. Thus, there is an urgent need to search for an agent for use in clinical and toxicity profile so that a randomized placebo control of SARS may be achieved by epidemiological measures, antiviral prophylaxis or treatment, and vaccination. During the last pandemic of SARS, the only available means for control were public health measures such as isolation of suspected cases, quarantine of contacts, and personal protective infection control procedures for high-risk individuals such as health care workers. There is an urgent need to find effective antiviral agents with acceptable side effect profiles. In developing countries such as China, commercially available western medicine with antiviral effects is unlikely to be affordable by most people. Moreover, the SARS mortality of Mainland China was only 7% which compared favorably with the 15 to 27% of other areas. Control trials can be conducted if the epidemic recurs in the coming winter.

3. SUMMARY OF THE INVENTION

The present invention is based in part on the surprising discovery that the biologically active compound baicalin and its derivatives, extracted and purified from a Chinese medicinal herb *Scutellaria baicalensis* Georgi (Chinese name: Huang Qin), exhibit potent antiviral activity against strains of coronavirus that infect humans and other animals, particularly at least 10 strains of hSARS virus, which belong to the order Nidovirales of the family Coronaviradae, based on neutralization test and plaque reduction assay. These strains include M39849, M36871, M65189, M67349, M70221, M71749, M51776, M61576, and M61565. In a specific embodiment, the hSARS virus is that which was deposited with the China Center for Type Culture Collection (CCTCC) on Apr. 2, 2003 and accorded an accession number, CCTCC-V200303.

It is estimated that approximately 50 percent of the thousands of drugs commonly used and prescribed today are either derived from a plant source or contain chemical imitations of a plant compound (Mindell, E. R., *Earl Mindell's Herb Bible, A Fireside Book* (1992)). Currently, a number of medicinal formulations contain herbal components or extracts from herbs. An herb is a small, non-woody (i.e., fleshy stemmed), annual or perennial seed-bearing plant in which all of the aerial parts die back at the end of each growing season. As the word is more generally used and as it is used herein, an herb is any plant or plant part which has a medicinal use. Thus, the term "herb" is also generally used to refer to the seeds, leaves, stems, flowers, roots, berries, bark or any other plant parts that are used for obtaining abstracts for healing.

Herbal medicines have been used for treating various diseases of humans and animals, and are available in many forms, including capsules, tablets or coated tablets; pellets; extracts or tinctures; powders; fresh or dried plants or plant parts; prepared teas; juices; creams and ointments; essential oils; or, as combinations of any of these forms. Herbal medications are administered by any one of various methods, including orally, rectally, parenterally, enterally, transdermally, intravenously, via feeding tubes, and topically.

The present invention is directed to a purified form of baicalin or its derivatives, which is extracted from a traditional Chinese herb (e.g., *Scutellaria baicalensis* Georgi, Chinese name: Huang Qin). The present invention discloses a treatment for viruses that belong to the order Nidovirales of the family Coronaviridae, such as hSARS, based on baicalin, a compound that exhibits potent antiviral activity against hSARS virus. The invention is useful in both clinical and scientific research applications.

Baicalin is a naturally occurring compound with a molecular weight of 446.38. It is less toxic than many available antiviral agents. The present discovery suggests that baicalin and its derivatives represent a novel class of compounds with potential for the development of safe drugs for therapy of diseases associated with viruses that belong to the order Nidovirales of the family Coronaviridae, such as SARS infection or other related infections.

As used herein, the term "baicalin compounds" refers to baicalin and its derivatives, as represented in Formula (I), and can comprise the raw material of baicalin, or extracts, derivatives or components of the same. In one embodiment, the therapeutic method of the present invention provides administration of a therapeutic agent comprising baicalin or its derivatives. In another embodiment, the therapeutic agent further comprises a steroid or other herbal medicines. In another embodiment, the present invention also provides a method of treatment further comprising administration of immunogenic formulations and vaccine preparations to a subject. In a specific embodiment, the immunogenic formulations or vaccine preparations of the present invention comprise live but attenuated viruses in the order Nidovirales of the family Coronaviridae, with or without adjuvants or anti-viral agents. In another specific embodiment, the immunogenic formulations or vaccine preparations comprise an inactivated or killed viruses in the order Nidovirales of the family Coronaviridae, with or without adjuvants or anti-viral agents.

In another aspect, the present invention provides pharmaceutical compositions comprising baicalin or its derivatives and a pharmaceutically acceptable vehicle. In a specific embodiment, the pharmaceutically acceptable vehicle comprises a carrier. In another specific embodiment, the pharmaceutically acceptable vehicle comprises an inactive vehicle such as an excipient. The present invention also provides kits containing a pharmaceutical composition of the present invention.

3.1 Definitions

As used herein, the term "analog" in the context of a non-proteinaceous analog refers to a second organic or inorganic molecule which possesses a similar or identical function as a first organic or inorganic molecule and is structurally similar to the first organic or inorganic molecule.

As used herein, the terms "antibody" and "antibodies" refer to monoclonal antibodies, polyclonal antibodies, bispecific antibodies, multispecific antibodies, human antibodies, humanized antibodies, chimeric antibodies, camelised antibodies, single domain antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

As used herein, the term "antigenicity" refers to the ability of a substance (e.g., foreign objects, microorganisms, drugs, antigens, proteins, peptides, polypeptides, nucleic acids, DNA, RNA, etc.) to trigger an immune response in a particular organism, tissue, and/or cell. Sometimes, the term "antigenic" is synonymous with the term "immunogenic".

As used herein, the term "baicalin compositions" refers to baicalin and its derivatives, as represented by Formula I.

As used herein, the term "derivative" in the context of a non-proteinaceous derivative refers to a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated.

As used herein, the terms "herb" and "herbal" refer to small, non-woody (i.e., fleshy stemmed), annual or perennial seed-bearing plants in which all of the aerial parts die back at the end of each growing season. As the word is more generally used and as it is used herein, an herb is any plant or plant part which has a medicinal use. Thus, the term "herb" is also generally used to refer to the seeds, leaves, stems, flowers, roots, berries, bark or any other plant parts that are used for obtaining abstracts for healing. The term "herbal" is used to refer to that which is derived from, or has as its source, one or more herbs.

As used herein, the term "hybridizes under stringent conditions" describes conditions for hybridization and washing under which nucleotide sequences having at least 30%, at least 35%, at least 40%, at least 45%, at least 50%, at least 55%, at least 60%, at least 65%, at least 70%, at least 75%, at least 80%, at least 85%, at least 90%, or at least 95% identity to each other typically remain hybridized to each other. Such hybridization conditions are described in, for example but not limited to, Current Protocols in Molecular Biology, John Wiley & Sons, N.Y. (1989), 6.3.1-6.3.6; Basic Methods in Molecular Biology, Elsevier Science Publishing Co., Inc., N.Y. (1986), pp. 75-78, and 84-87; and Molecular Cloning, Cold Spring Harbor Laboratory, N.Y. (1982), pp. 387-389, and are well known to those skilled in the art. A preferred, non-limiting example of stringent hybridization conditions is hybridization in 6× sodium chloride/sodium citrate (SSC), 0.5% SDS at about 68° C. followed by one or more washes in 2×SSC, 0.5% SDS at room temperature. Another preferred, non-limiting example of stringent hybridization conditions is hybridization in 6×SSC at about 45° C. followed by one or more washes in 0.2×SSC, 0.1% SDS at about 50-65° C.

As used herein, the term "immunogenicity" refers to the ability of a substance (e.g., foreign objects, microorganisms, drugs, antigens, proteins, peptides, polypeptides, nucleic acids, DNA, RNA, etc.) to evoke an immune response within an organism. Immunogenicity depends partly upon the size of the substance in question and partly upon how unlike the host molecules is the substance. Highly conserved proteins tend to have rather low immunogenicity.

As used herein, the term "mutant" refers to the presence of mutations in the nucleotide sequence of an organism as compared to a wild-type organism.

As used herein, the term "pharmaceutically active agent" refers to any medically useful substance, including any therapeutically beneficial substance which may be used in combination with the purified baicalin or its derivative or composition of the present invention, including, but not limited to: viricides; microbicides; antibiotics; amino acids; peptides; vitamins; co-factors for protein synthesis; hormones including growth hormones; endocrine tissue; living cells including for example: stem cells, chondrocytes, bone marrow cells, and parenchymal cells; synthesizers; enzymes; biocompatible surface active agents; antigenic agents; growth factors including but not limited to: transforming growth factor, and insulin like growth factor; immunosuppressants; and permeation enhancers.

As used herein, the terms "subject" and "patient" are used interchangeably. As used herein, the terms "subject" and "subjects" refer to an animal, preferably a mammal including a non-primate (e.g., cows, pigs, horses, goats, sheep, cats, dogs, ferrets, ferret badgers, rabbits, raccoon dogs, civets, avian species and rodents) and a primate (e.g., monkeys such as a cynomolgous monkey and humans), and more preferably a human.

As used herein, the term "variant" refers either to a naturally occurring genetic mutant of hSARS virus or a recombinantly prepared variation of hSARS virus each of which contain one or more mutations in its genome compared to the hSARS virus of CCTCC-V200303. The term "variant" may also refer to either a naturally occurring variation of a given peptide or a recombinantly prepared variation of a given peptide or protein in which one or more amino acid residues have been modified by amino acid substitution, addition, or deletion.

As used herein, the term "vehicle" refers to a substance that facilitates the use of a drug, pigment, or other material mixed with it. The *New Oxford American Dictionary* (2001).

As used herein, the term "carrier" refers to a substance used to support or convey another substance such as a pigment, catalyst, or radioactive material. The *New Oxford American Dictionary* (2001).

As used herein, the term "excipient" refers to an inactive substance that serves as the vehicle or medium for a drug or other active substance. The *New Oxford American Dictionary* (2001). Excipients are inert substances which are commonly used as a diluent, vehicle, preservatives, binders, or stabilizing agent for drugs and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See also Joseph P. Remington, *Remington's Pharmaceutical Sciences,* 18th ed., Mack Publishing Co., Easton, Pa.), which is hereby incorporated in its entirety.

As used herein, the term "—$(C_1$-$C_{10})$alkyl" refers to a saturated straight chain or branched non-cyclic hydrocarbon having from 1 to 10 carbon atoms. Representative saturated straight chain —$(C_1$-$C_{10})$alkyls include -methyl, -ethyl, -n-propyl, -n-butyl, -n-pentyl, -n-hexyl, -n-heptyl, -n-octyl, -n-nonyl, and -n-decyl. Representative saturated branched —$(C_1$-$C_{10})$alkyls include -isopropyl, -sec-butyl, -isobutyl, -tert-butyl, -isopentyl, -2-methylbutyl, -3-methylbutyl, -2,2-dimethylbutyl, -2,3-dimethylbutyl, -2-methylpentyl, -3-methylpentyl, -4-methylpentyl, -2-methylhexyl, -3-methylhexyl, -4-methylhexyl, -5-methylhexyl, -2,3-dimethylbutyl, -2,3-dimethylpentyl, -2,4-dimethylpentyl, -2,3-dimethylhexyl, -2,4-dimethylhexyl, -2,5-dimethylhexyl, -2,2-dimethylpentyl, -2,2-dimethylhexyl, -3,3-dimethylpentyl, -3,3-dimethylhexyl, -4,4-dimethylhexyl, -2-ethylpentyl, -3-ethylpentyl, -2-ethylhexyl, -3-ethylhexyl, -4-ethylhexyl, -2-methyl-2-ethylpentyl, -2-methyl-3-ethylpentyl, -2-methyl-4-ethylpentyl, -2-methyl-2-ethylhexyl, -2-methyl-3-ethylhexyl, -2-methyl-4-ethylhexyl, -2,2-diethylpentyl, -3,3-diethylhexyl, -2,2-diethylhexyl, -3,3-diethylhexyl and the like.

As used herein, the term "—$(C_2$-$C_{10})$alkenyl" refers to a straight chain or branched non-cyclic hydrocarbon having from 2 to 10 carbon atoms and including at least one carbon-carbon double bond. Representative straight chain and branched —$(C_2$-$C_{10})$alkl-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

As used herein, the term "—$(C_2$-$C_{10})$alkynyl" refers to a straight chain or branched non-cyclic hydrocarbon having from 2 to 10 carbon atoms and including at least one carbon-carbon triple bond. Representative straight chain and branched —$(C_2$-$C_{10})$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl and the like.

As used herein, the term "—$(C_3$-$C_{10})$cycloalkyl" refers to a saturated cyclic hydrocarbon having from 3 to 10 carbon atoms. Representative $(C_3$-$C_8)$cycloalkyls include -cyclopropyl, -cyclobutyl, -cyclopentyl, -cyclohexyl, -cycloheptyl, -cyclooctyl, -cyclononyl and -cyclodecyl.

As used herein, the term "—$(C_8$-$C_{14})$bicycloalkyl" refers to a bi-cyclic hydrocarbon ring system having from 8 to 14 carbon atoms and at least one saturated cyclic alkyl ring. Representative —$(C_8$-$C_{14})$bicycloalkyls include -indanyl, -1,2,3,4-tetrahydronaphthyl, -5,6,7,8-tetrahydronaphthyl, -perhydronaphthyl and the like.

As used herein, the term "—$(C_8$-$C_{14})$tricycloalkyl" refers to a tri-cyclic hydrocarbon ring system having from 8 to 14 carbon atoms and at least one saturated cycloalkyl ring. Representative —$(C_8$-$C_{14})$tricycloalkyls include -pyrenyl, -1,2,3,4-tetrahydroanthracenyl, -perhydroanthracenyl, -aceanthreneyl, -1,2,3,4-tetrahydropenanthrenyl, -5,6,7,8-tetrahydrophenanthrenyl, -perhydrophenanthrenyl and the like.

As used herein, the term "—$(C_5$-$C_{10})$cycloalkenyl" refers to a cyclic non-aromatic hydrocarbon having at least one carbon-carbon double bond in the cyclic system and from 5 to 10 carbon atoms. Representative $(C_5$-$C_{10})$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl and the like.

As used herein, the term "—($C_8$-$C_{14}$)bicycloalkenyl" refers to a bi-cyclic hydrocarbon ring system having at least one carbon-carbon double bond in each ring and from 8 to 14 carbon atoms. Representative —($C_8$-$C_{14}$)bicycloalkenyls include -indenyl, -pentalenyl, -naphthalenyl, -azulenyl, -heptalenyl, -1,2,7,8-tetrahydronaphthalenyl and the like.

As used herein, the term "—($C_8$-$C_{14}$)tricycloalkenyl" refers to a tri-cyclic hydrocarbon ring system having at least one carbon-carbon double bond in each ring and from 8 to 14 carbon atoms. Representative —($C_8$-$C_{14}$)tricycloalkenyls include -anthracenyl, -phenanthrenyl, -phenalenyl, -acenaphthalenyl, -as-indacenyl, -s-indacenyl and the like.

As used herein, the term "—($C_{14}$)aryl" refers to a 14-membered aromatic carbocyclic moiety such as anthryl and phenanthryl.

As used herein, the term "-(3- to 5-membered)heterocycle" or "-(3- to 5-membered)heterocyclo" means a 3- to 5-membered monocyclic heterocyclic ring which is either saturated, unsaturated, non-aromatic or aromatic. A 3- or 4-membered heterocycle can contain up to 3 heteroatoms and a 5-membered heterocycle can contain up to 4 heteroatoms. Each heteroatom is independently selected from nitrogen, which can be quaternized; oxygen; and sulfur, including sulfoxide and sulfone. The -(3- to 5-membered)heterocycle can be attached via any heteroatom or carbon atom. Representative -(3- to 5-membered)heterocycles include furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl, tetrahydrothiophenyl and the like.

As used herein, the term "—CH(halo)$_2$" refers to a methyl group wherein two of the hydrogens of the methyl group have been replaced with a halogen. Representative —CH(halo)$_2$ groups include —CHF$_2$, —CHCl$_2$, —CHBr$_2$, —CHBrCl, —CHClI and —CHI$_2$.

As used herein, the term "—C(halo)$_3$" refers to a methyl group wherein each of the hydrogens of the methyl group has been replaced with a halogen. Representative —C(halo)$_3$ groups include —CF$_3$, —CF$_2$Cl, —CCl$_3$, —CBr$_3$, —CFBr$_2$ and —CI$_3$.

As used herein, the term "counterion" refers to a positively-charged moiety and includes ammonium and the cations of alkali metals such as sodium, potassium and lithium; alkaline earth metals such as calcium and magnesium; other metals, such as aluminum and zinc; organic amines, such as unsubstituted or hydroxy-substituted mono-, di- or trialkylamines; dicyclohexylamine; tributyl amine; pyridine; N-methyl-N-ethylamine; diethylamine; triethylamine; mono-, bis- or tris-(2-hydroxy-lower alkyl amines), such as mono-, bis- or tris-(2-hydroxyethyl)amine, 2-hydroxy-tert-butylamine or tris-(hydroxymethyl)methylamine; N,N-di-lower alkyl-N-(hydroxy lower alkyl)-amines, such as N,N-dimethyl-N-(2-hydroxyethyl)amine or tri-(2-hydroxyethyl)amine; N-methyl-D-glucamine; and amino acids such as arginine, lysine and the like.

As used herein, the term "halo" includes F, Cl, Br and I.

As used herein, the phrase "pharmaceutically acceptable salt" is a salt formed from an acid and a basic nitrogen group of one of the Compounds of Formula (I). Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. The term "pharmaceutically acceptable salt" also refers to a salt prepared from a Compound of Formula (I) having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia and organic amines, such as unsubstituted or hydroxy-substituted mono-, di- or trialkylamines; dicyclohexylamine; tributyl amine; pyridine; N-methyl-N-ethylamine; diethylamine; triethylamine; mono-, bis- or tris-(2-hydroxy-lower alkyl amines), such as mono-, bis- or tris-(2-hydroxyethyl)amine, 2-hydroxy-tert-butylamine or tris-(hydroxymethyl)methylamine, N,N-di-lower alkyl-N-(hydroxy lower alkyl)-amines, such as N,N-dimethyl-N-(2-hydroxyethyl)amine or tri-(2-hydroxyethyl)amine; N-methyl-D-glucamine; and amino acids such as arginine, lysine and the like.

4. DESCRIPTION OF THE FIGURES

Figure 3:
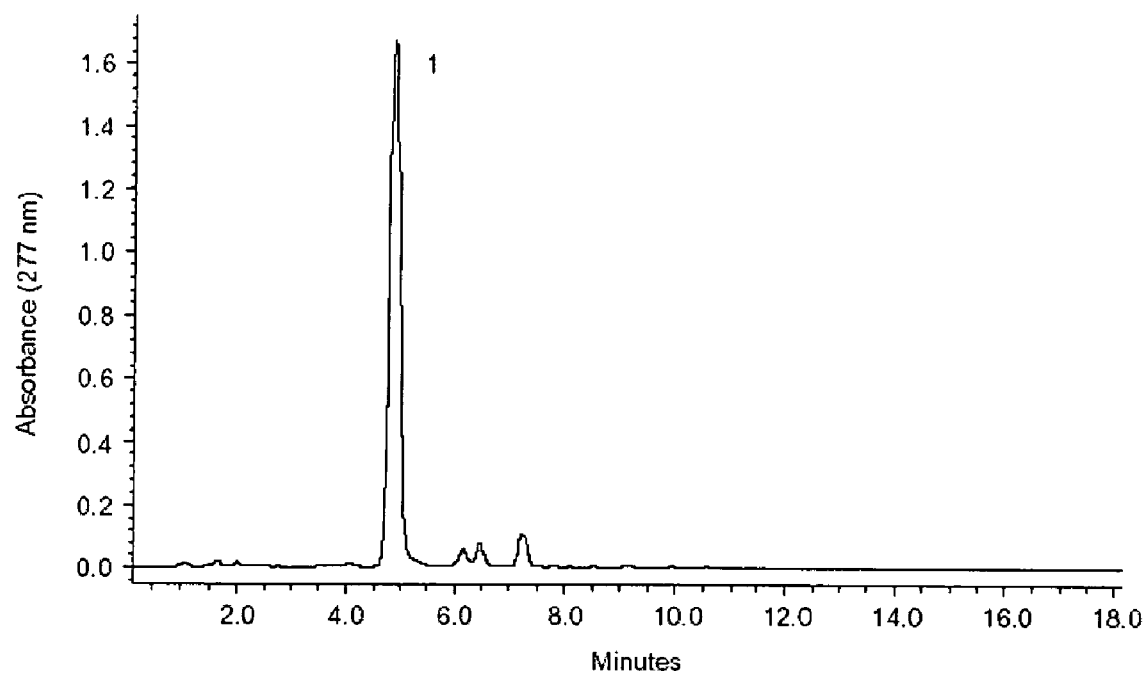

FIG. 3 shows a HPLC chromatogram of baicalin purified by the preparative HSCCC: 1=baicalin. Experimental conditions: column—reversed-phase symmetry $C_{18}$ column (150× 3.9 mm i.d., 5 µm); column temperature—30° C.; mobile phase—0.1% phosphoric acid (A) and acetonitrile (B), linear gradient elution—A-B (75:25, v/v) to A-B (45:55, v/v) in 15 min, then to initial condition A-B (75:25, v/v) immediately; flow-rate—1.0 ml min$^{-1}$; detection—277 nm; injection volume—20 µl. The first separation by HSCCC resulted in baicalin with 82.0% purity.

Figure 4:
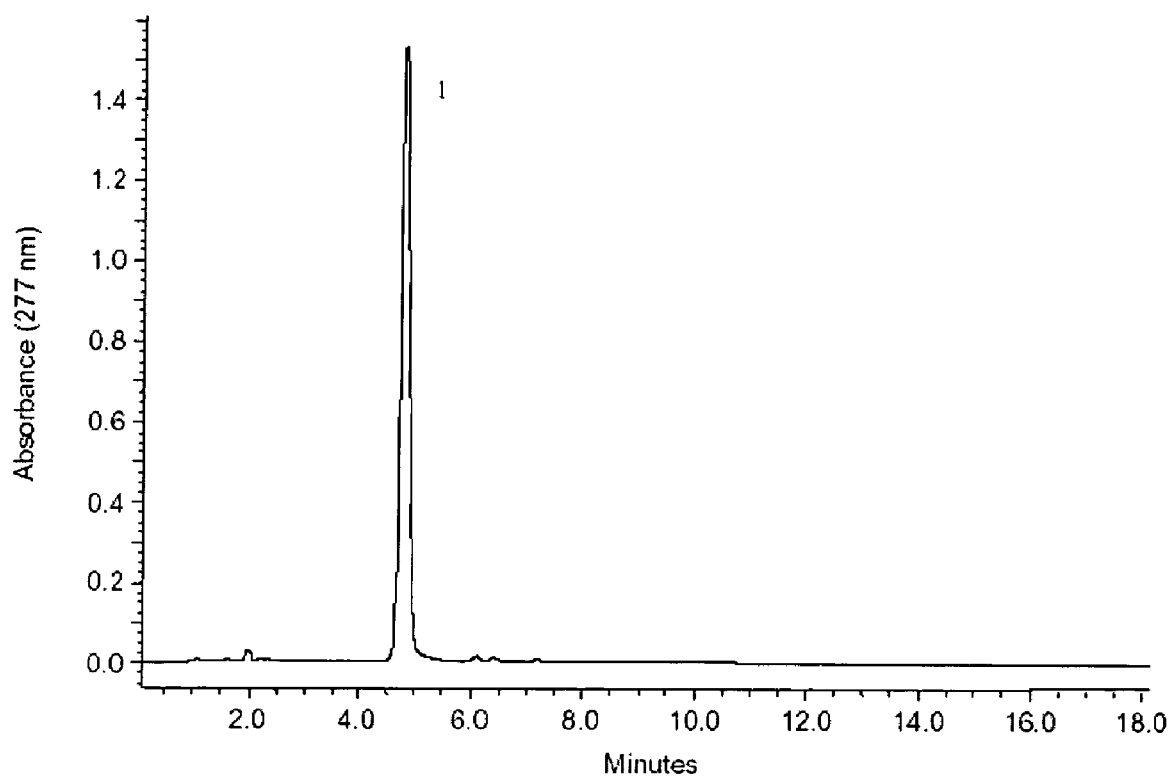

FIG. 4 shows a HPLC chromatogram of baicalin purified by the preparative HSCCC for the second time, which resulted in baicalin with 96.5% purity.

5. DETAILED DESCRIPTION OF THE INVENTION

The present invention relates to therapeutic agents useful for the treatment of diseases associated with the order Nidovirales of the family Coronaviradae, such as Severe Acute Respiratory Syndrome (SARS) in humans and other animals. The therapeutic agents of the present invention relate to highly purified forms of baicalin and its derivatives, extracted and purified from the Chinese medicinal plant *Scutellaria baicalensis* Georgi (Chinese name: Huang Qin), that exhibits potent antiviral activity against members of Coronaviradae that infects humans; in particular, the virus causing Severe Acute Respiratory Syndrome (SARS) in humans ("hSARS virus"). The invention also relates to a therapeutic method, using therapeutics comprising baicalin, for the treatment, amelioration, management or prevention of diseases associated with members of Coronaviradae that infect animals, which include at least human; in particular, the members of Coronaviradae that are strains of the hSARS virus.

5.1 Therapeutic Agents Comprising Baicalin and/or its Derivatives

Baicalin is a naturally occurring chemical compound purified from traditional Chinese herbs (e.g., *Scutellaria*

*baicalensis* Georgi, Chinese name: Huang Qin) known to have antimicrobial activities. Baicalin is a less expensive alternative for antiviral prophylaxis or treatment.

The present invention encompasses baicalin and its derivatives, i.e., compounds of Formula (I):

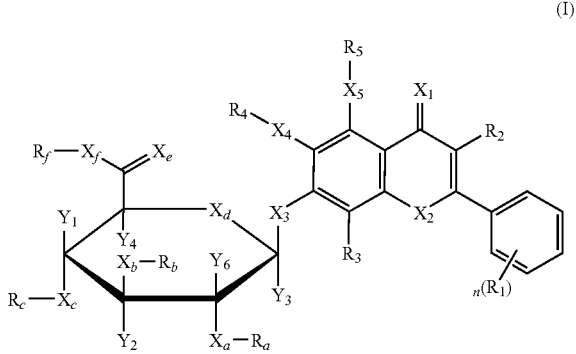

(I)

wherein each of $X_1$, $X_2$, $X_3$, $X_4$, $X_5$, $X_a$, $X_b$, $X_c$, $X_d$, $X_e$ and $X_f$ is independently O or S;

each of $R_4$, $R_5$, $R_a$, $R_b$ and $R_c$ is independently H, $(C_1\text{-}C_{10})$ alkyl optionally substituted with 1-5 $R_y$ groups, or $(C_1\text{-}C_{10})$ alkyl-O—$(C_1\text{-}C_{10})$alkyl, each $(C_1\text{-}C_{10})$alkyl of which is optionally substituted with 1-5 $R_y$ groups;

each $R_y$ is independently $R_q$ or —$(C_2\text{-}C_{10})$alkenyl, —$(C_2\text{-}C_{10})$alkynyl, —$(C_3\text{-}C_{10})$cycloalkyl, —$(C_8\text{-}C_{14})$bicycloalkyl, —$(C_8\text{-}C_{14})$tricycloalkyl, —$(C_5\text{-}C_{10})$cycloalkenyl, $(C_8\text{-}C_{14})$bicycloalkenyl, —$(C_8\text{-}C_{14})$tricycloalkenyl, -phenyl, -naphthyl or —$(C_{14})$aryl, each or which is unsubstituted or substituted with one or more $R_z$ groups;

each of $R_1$, $R_2$ and $R_3$ is independently $R_q$ or —$(C_1\text{-}C_{10})$ alkyl, —$(C_2\text{-}C_{10})$alkenyl, —$(C_2\text{-}C_{10})$alkynyl, —$(C_3\text{-}C_{10})$cycloalkyl, —$(C_8\text{-}C_{14})$bicycloalkyl, —$(C_8\text{-}C_{14})$tricycloalkyl, —$(C_5\text{-}C_{10})$cycloalkenyl, $(C_8\text{-}C_{14})$bicycloalkenyl, —$(C_8\text{-}C_{14})$tricycloalkenyl, -phenyl, -naphthyl or —$(C_{14})$aryl, each or which is unsubstituted, substituted with one or more $R_q$ groups, substituted with one or more $R_z$ groups, or substituted with one or more $R_q$ groups and one or more $R_z$ groups;

$R_f$ is H, $(C_1\text{-}C_{12})$alkyl optionally substituted with 1-5 $R_y$ groups, $(C_1\text{-}C_{12})$alkyl-O—$(C_1\text{-}C_{12})$alkyl, each $(C_1\text{-}C_{12})$ alkyl of which is optionally substituted with 1-5 $R_y$, or a counterion;

each $R_q$ is independently CN, OH, halo, $N_3$, $NO_2$, $N(R_z)_2$, =$NR_z$, CH=$NR_z$, $NR_z$OH, $OR_z$, $COR_z$, $C(O)OR_z$, $OC(O)$ $R_z$, $OC(O)OR_z$, $SR_z$, $S(O)R_z$ or $S(O)_2R_z$;

each $R_z$ is independently —$(C_1\text{-}C_6)$alkyl, —$(C_2\text{-}C_6)$alkenyl, $(C_2\text{-}C_6)$alkynyl, $(C_3\text{-}C_8)$cycloalkyl, —$(C_5\text{-}C_8)$cycloalkenyl, -phenyl, -(3- to 5-membered)heterocycle, $C(halo)_3$ or —$CH(halo)_2$; and n is 0, 1, 2, 3, 4 or 5.

Certain Compounds of Formula (I) may have asymmetric centers and therefore exist in different enantiomeric and diastereomeric forms. A Compound of Formula (I) can be in the form of an optical isomer or a diastereomer. Accordingly, the invention encompasses Compounds of Formula (I) and their uses as described herein in the form of their optical isomers, diastereomers and mixtures thereof, including a racemic mixture.

One or more hydrogen, carbon or other atoms of a Compound of Formula (I) can be replaced by an isotope of the hydrogen, carbon or other atoms. Such compounds, which are encompassed by the present invention, are useful as research and diagnostic tools in metabolism pharmacokinetic studies and in binding assays.

In one preferred embodiment, one or more of $X_1$, $X_2$, $X_3$, $X_4$, $X_5$, $X_a$, $X_b$, $X_c$, $X_d$, $X_e$ and $X_f$ is O.

In another preferred embodiment, one or more of $R_a$, $R_b$, $R_c$, $R_f$, $R_1$, $R_2$, $R_3$, $R_4$, $R_5$ is H.

In another preferred embodiment, one or more of $Y_1$, $Y_2$, $Y_3$, $Y_4$ and $Y_6$ is H.

In another preferred embodiment, one or more of $Y_1$, $Y_2$, $Y_3$, $Y_4$ and $Y_6$ is $CH_3$.

In another preferred embodiment, $R_1$ is $CH_3$.

In another preferred embodiment, n is 5.

In another preferred embodiment, the therapeutic agent of the present invention comprises baicalin represented by the following Formula (II):

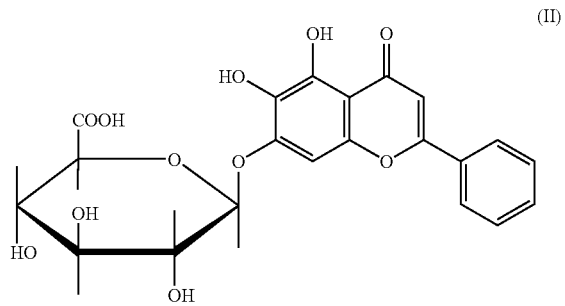

(II)

Although an oral dose of 1.5 gm of baicalin can only achieve a serum concentration of 0.47 µg/ml, intravenous administration of a 360 mg dose of baicalin in human can achieve a peak serum concentration of 74 µg/ml. Thus intravenous baicalin should be considered for treatment in randomized placebo control trials in developing countries where such formulations are available and affordable.

The baicalin compositions that are useful for the present invention may be prepared by various methods, such as by extraction, boiling with water, dissolution in organic solvents such as alcohols, separation techniques using chromatological methods, and supercritical $CO_2$ fluid extraction, etc. In one embodiment, the baicalin compositions can be prepared by extracting a raw material of baicalin or its derivatives. For example, the raw material can first be collected. Optionally, such raw material can be subjected to cleaning or drying or both, before the extraction. The raw material can then be processed to obtain the baicalin compositions. For example, and not by way of limitation, powder comprising the baicalin compositions can be boiled with water and filtered. The filtrate can then be added with water to the desired concentration, and the preparation can then be sterilized and used for injection.

In another embodiment, the baicalin compositions can be prepared by immersion in alcohols such as ethanol, wherein the immersion time in ethanol is sufficiently long enough to release the baicalin compositions from their source. It will be appreciated that there are other methods of preparing the baicalin compositions that are within the scope of the present invention.

Further, the extracts of plants belonging to *Scutellaria baicalensis* Georgi may be obtained advantageously from the adult form of these plants, but can also be extracted from the dried mature fruit. The extracts of plants belonging to the *Scutellaria baicalensis* Georgi may be obtained from the seeds, flowers, stems, leaves and/or roots of these plants.

When preparing the extracts of plants belonging to the *Scutellaria baicalensis* Georgi, any methods generally used when extracting plant-derived extracts can be used. That is, a plant belonging to *Scutellaria baicalensis* Georgi may be used for solvent extraction in the fresh state, or, if desired, dried and then used as is or pulverized to form a powder. The solvent used for extraction may be any conventional solvent generally usable when extracting the ingredients of a plant from the plant, and is not particularly limited.

For example, the extract derived from the *Scutellaria baicalensis* Georgi plant material, such as the fruit, seeds, leaves, flowers, stems or roots, may be a water/water-miscible organic solvent extract. The organic solvent ultimately employed must not disrupt the active ingredient baicalin of the present invention. For example, some components may be only sparingly soluble in water. The ratio of water to water-miscible organic solvent is generally in the order of 0.5% to 70% v/v water-miscible organic solvent (such as methanol, ethanol, propanol, propylene glycol, erythrite, butanol, butanediol, acetonitrile, ethyleneglycol, glycidol, glycerol dihydroxyacetone or acetone).

The extract in this regard may be prepared by exposing the *Scutellaria baicalensis* Georgi plant material to the water/water-miscible solvent mix. The exposure time in general terms is indirectly proportional to the temperature of the mixture. The temperature of the mixture may range, for example, from ambient temperature to boiling temperature. Exposure time may be between, for example, 5 minutes to several days.

Undesired components may be removed from the extract to give a final *Scutellaria baicalensis* Georgi plant extract as utilized herein by standard procedures. Examples include chromatographic techniques, such as preparative high performance liquid chromatography (HPLC) using UV detection. Examples of chromatographic media include inorganic materials such as porous silica; controlled poreglass apatite, fluoroapatite, aluminum oxide, composite materials such as coated silica and coated polystyrene; and synthetic polymers such as polyacrylamide, polymethacrylate, and polystyrene. The solvent phase for chromatographic separation may be an organic solvent such as methanol, ethanol, propanol, butanol, pentanol, acetone, butanone, chloroform, dichloromethane, dichloroethane, dichlorobutane, ethylacetate, ether or dimethyl sulphoxide, which may be used to dissolve the extract.

In a specific embodiment, baicalin is separated and purified from *Scutellaria baicalensis* Georgi by high-speed counter-current chromatography (HSCCC) as described in "Application of high-speed counter-current chromatography to the preparative separation and purification of baicalin from the Chinese medicinal plant *Scutellaria baicalensis*" (by Lu et al., 2003, *J Chromatogr A* 1017:117-123), which is hereby incorporated by reference in its entirety. Thus, in a preferred embodiment, the present invention provides a compound consisting essentially of baicalin or compound represented by Formula (II). As used herein, the term "consisting essentially of baicalin or compound represented by Formula (II)" refers to a purified baicalin, having at least about 80%, at least about 82%, at least about 84%, at least about 85%, at least about 86%, at least about 88%, at least about 90%, at least about 92%, at least about 94%, at least about 95%, at least about 96%, at least about 97%, at least about 98%, or at least about 99% purity. Also see FIGS. 3 and 4 and Section 6, infra.

Methods for obtaining compounds within the scope of Formula (I) are well known to those skilled in the art having the benefit of present disclosure before them. More particularly, any of the compounds within the scope of Formula (I) can be obtained in a useful form by appropriate adaptation of within described method for obtaining baicalin itself, such as extraction and/or simple chemical modifications, well known to those with ordinary skill in the art, of baicalin followed by purification using HSCCC.

In another embodiment, the baicalin composition can be prepared by mixing the baicalin with one or more pharmaceutically acceptable vehicles, such as carriers, excipients, auxiliaries and/or diluents.

Furthermore, the present invention provides pharmaceutical compositions comprising the compounds of the present invention and additionally, anti-viral agents together with one or more pharmaceutically acceptable vehicles. The present invention also provides pharmaceutical compositions comprising the compounds of the present invention, and further, other pharmaceutical compositions comprising other herbal medicines, and optionally, steroids. The present invention also provides kits comprising pharmaceutical compositions of the present invention.

5.2 Methods of Treating Disease Associated with the Order Nidovirales of the Family Coronaviridae The method of the present invention relates to treatment of a disease associated with a virus that belongs to the order Nidovirales of the family Coronaviradae, which infects humans and other animals. The virus may comprise a nucleic acid sequence that hybridizes under stringent conditions to the sequence.

In another embodiment, the method of the present invention provides the use of baicalin and/or its pharmaceutically acceptable derivatives and/or salts. The methods may further comprise the co-administration of vaccine preparations comprising viruses belonging to the order Nidovirales of the family Coronaviradae, including recombinant and chimeric forms of said viruses, or subunits of the viruses. In a specific embodiment, the vaccine preparations comprise live but attenuated viruses belonging to the order Nidovirales of the family Coronaviradae, with or without pharmaceutically acceptable excipients, including adjuvants. In another specific embodiment, the vaccine preparations comprise inactivated or killed viruses belonging to the order Nidovirales of the family Coronaviradae, with or without pharmaceutically acceptable excipients, including adjuvants.

In specific embodiments, the methods of the present invention is effective for hSARS virus comprising sequences deposited with GenBank® having accession nos. NC_004718, AY304495, AY304494, AY304493, AY304492, AY304491, AY304490, AY304489, AY304488, AY304487, AY304486, AY360146, AY278491, AY310120, AY278489, AY362699, AY362698, AY283798, AY283797, AY283796, AY283795, AY283794, AY268070, AY278741, AY340092, AY351680, AP006561, AP006560, AP006559, AP006558, AP006557, AY278554, AY348314, AY338175, AY338174, AY323977, AY322199, AY322198, AY322197, AH013000, AY322208, AY322207, AY322206, AY322205, AH012999, AY321118, AY323976, AY323975, AY323974, AY286320, AY290752, AY291315, AY307165, AY279354, AY278490, AY278487, AY297028, AY286402, AY274119, AY291451, AY271716, AY282752, AY278488, AY268049, AY269391, all of which are incorporated herein by reference in their entireties.

Furthermore, the present invention provides methods for treating, ameliorating, managing, or preventing diseases caused by Coronavirus, including SARS, by administering baicalin and/or its pharmaceutically acceptable derivatives and/or salts and vaccine preparations or antibodies of the present invention alone or in combination with other herbal compositions, antiviral agents (e.g., amantadine, rimantadine, gancyclovir, acyclovir, ribavirin, penciclovir, oseltamivir, foscarnet zidovudine (AZT), didanosine (ddI), lamivudine (3TC), zalcitabine (ddC), stavudine (d4T), nevirapine, delavirdine, indinavir, ritonavir, vidarabine, nelfinavir, saquinavir, relenza, tamiflu, pleconaril, interferons, etc. as well as an antibody which immunospecifically binds to a target virus), steroids and corticosteroids such as prednisone, cortisone, fluticasone and glucocorticoid, antibiotics, analgesics, bronchodilators, or other treatments for respiratory and/or viral infections. The vaccine preparations, antibodies, herbal compositions, antivirals, steroids, corticosteroids, antibiotics, analgesics, bronchodilators, and other therapeutic agents for respiratory infections can be co-administered concurrently, or sequentially.

The present invention provides treatment, amelioration, management and prevention of disease associated with the order Nidovirales of the family Coronaviradae, that affects animals, which include at least human. In specific embodiments, the virus is hSARS virus. The invention also relates to administration of baicalin intravenously, rectally, parenterally, enterally, transdermally, via feeding tubes, and topically.

5.3 Vaccines

The invention also provides vaccine formulations for the prevention and treatment of infections in addition of administering therapeutic compounds comprising baicalin and/or its derivatives. In certain embodiments, the vaccine of the invention comprises hSARS virus. In certain embodiments, the virus is attenuated, inactivated, or killed.

In certain embodiments, the vaccine of the invention further comprises recombinant and chimeric viruses of the SARS virus. In certain embodiments, the virus is attenuated, inactivated, or killed. In other embodiments, the baicalin compositions of the present invention are used in combination with one or more steroids to treat diseases caused by viruses that belong to the order Nidovirales of the family Coronaviradae, such as hSARS virus.

In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG and *Corynebacterium parvum*.

The vaccines of the invention may be multivalent or univalent. Multivalent vaccines are made from recombinant viruses that direct the expression of more than one antigen.

In another aspect, the methods of the present invention also provides administration of DNA vaccine formulations comprising a nucleic acid or fragment of the hSARS virus in combination with administration of baicalin and/or its derivatives. In another specific embodiment, the DNA vaccine formulations useful for the present invention comprise a nucleic acid or fragment thereof encoding the antibodies which immunospecifically binds hSARS viruses. In DNA vaccine formulations, a vaccine DNA comprises a viral vector, such as that derived from the hSARS virus, bacterial plasmid, or other expression vector, bearing an insert comprising a nucleic acid molecule of the present invention operably linked to one or more control elements, thereby allowing expression of the vaccinating proteins encoded by said nucleic acid molecule in a vaccinated subject. Such vectors can be prepared by recombinant DNA technology as recombinant or chimeric viral vectors carrying a nucleic acid molecule of the hSARS virus.

Many methods may be used to introduce the vaccine formulations described above. These include, but are not limited to, oral, intradermal, intramuscular, intraperitoneal, intravenous, subcutaneous, intranasal routes, and via scarification (scratching through the top layers of skin, e.g., using a bifurcated needle).

The patient to which the vaccine is administered is preferably a mammal, most preferably a human, but can also be a non-human animal including but not limited to cows, horses, sheep, pigs, rabbits, raccoons, raccoon dogs, ferrets, ferret badgers, civets, avians, fowl (e.g., chickens), goats, cats, dogs, hamsters, mice and rats.

5.4. Assay for Determining Efficacy and Dosage of Baicalin and its Derivatives as a Therapeutic Agent Whether a particular treatment of the invention is effective to treat SARS can be determined by any method known in the art, for example but not limited to, those methods described in this section.

The safety and efficiency of the proposed method of treatment may be tested in the course of systematic medical and biological assays on animals, toxicological analyses for acute and systemic toxicity, histological studies and functional examinations, and clinical evaluation of patients having a variety of indications for SARS.

The efficacy of the method of the present invention may be tested in appropriate animal models, and in human clinical trials, by any method known in the art. For example, the animal or human subject may be evaluated for any indicator of SARS that the method of the present invention is intended to treat. The efficacy of the method of the present invention for treatment of SARS can be assessed by measuring the levels of nucleic acid molecules, proteins of the hSARS virus in the animal model or human subject at suitable time intervals before, during, or after treatment. Any change or absence of change can be identified and correlated with the effect of the treatment on the subject.

The invention provides methods for the identification of a compound that inhibits the ability of hSARS virus to infect a host or a host cell. In certain embodiments, the invention provides methods for the identification of a baicalin derivative that reduces the ability of hSARS virus to replicate in a host or a host cell. Any technique well-known to the skilled artisan can be used to screen for a baicalin derivative that would abolish or reduce the ability of hSARS virus to infect a host and/or to replicate in a host or a host cell.

In certain embodiments, the invention provides methods for the identification of a compound that inhibits the ability of hSARS virus to replicate in a mammal or a mammalian cell. More specifically, the invention provides methods for the identification of a compound that inhibits the ability of hSARS virus to infect a mammal or a mammalian cell. In certain embodiments, the invention provides methods for the identification of a compound that inhibits the ability of hSARS virus to replicate in a mammalian cell. In a specific embodiment, the mammalian cell is a human cell.

In another embodiment, a cell is contacted with a test compound and infected with the hSARS virus. In certain embodiments, a control culture is infected with the hSARS virus in the absence of a test compound. The cell can be contacted with a test compound before, concurrently with, or subsequent to the infection with the hSARS virus. In a specific embodiment, the cell is a mammalian cell. In an even more specific embodiment, the cell is a human cell. In certain embodiments, the cell is incubated with the test compound for at least 1 minute, at least 5 minutes, at least 15 minutes, at least 30 minutes, at least 1 hour, at least 2 hours, at least 5 hours, at least 12 hours, or at least 1 day. The titer of the virus can be measured at any time during the assay. In certain embodiments, a time course of viral growth in the culture is determined. If the viral growth is inhibited or reduced in the presence of the test compound, the test compound is identified as being effective in inhibiting or reducing the growth or infection of the hSARS virus. In a specific embodiment, the compound that inhibits or reduces the growth of the hSARS virus is tested for its ability to inhibit or reduce the growth rate of other viruses to test its specificity for the hSARS virus.

In one embodiment, a test compound is administered to an animal and the animal is infected with the hSARS virus. In certain embodiments, a control animal is infected with the hSARS virus without the administration of a test compound. The test compound can be administered before, concurrently with, or subsequent to the infection with the hSARS virus. In a specific embodiment, the animal is a mammal. In an even more specific embodiment, the model animal can be, but is not limited to, a cotton rat, a mouse, or a monkey. The titer of the virus in the model animal can be measured at any time during the assay. In certain embodiments, a time course of viral growth in the culture is determined. If the viral growth is inhibited or reduced in the presence of the test compound, the test compound is identified as being effective in inhibiting or reducing the growth or infection of the hSARS virus. In a specific embodiment, the compound that inhibits or reduces the growth of the hSARS virus in the animal is tested for its ability to inhibit or reduce the growth rate of other viruses to test its specificity for the hSARS virus.

Efficacy and dose of the therapeutic agents of the present invention can be determined as shown in Section 6, infra. The procedures require (1) neutralization test and (2) plaque reduction assay. The procedure used for in-vitro antiviral susceptibility testing are as follows: the in-vitro susceptibility against the prototype hSARS virus is performed in 96-well microtitre plates seeded with fetal rhesus kidney-4 cells. Two-fold dilutions of antiviral agents starting from more than 4 times the peak serum concentration after the maximum therapeutic dose to less than one-quarter of the trough serum concentration are tested in quadruplicate against 100 TCID50 of hSARS virus. A corresponding set of cell controls with drug but without virus inoculation should be used as controls for drug toxicity.

The cells should then be scored for the inhibition of the cytopathic effect (CPE) at 48 hours and at 72 hours. Their antiviral activities may also be compared in both fRHK-4 and Vero-E6 cell lines. Those likely to have clinically significant inhibitory activity should be tested by the plaque reduction assay.

For the plaque reduction assay, it is necessary to prepare a 24-well tissue culture plates with a confluent cell monolayer ($1 \times 10^5$ cells per well) in 1.0 ml of minimal essential medium (MEM) with 10% fetal calf serum (FCS). After the medium is aspirated, 50-100 plaque forming units (PFU) of SARS associated coronavirus (in 1% FCS/MEM containing antivirals at appropriate concentrations) should be added to each well. Plates should be incubated for 2 hours at 37° C. in 5% CO2. The inoculum should be aspirated and 1.0 ml of overlay (1.0% low-melting point agarose in 1% FCS/MEM with corresponding drug dilutions) added to each well.

Plates should be further incubated for 48 hours at 37° C. in 5% CO2. Cells are then fixed by adding 2 ml of 10% formaldehyde and incubating the plates at room temperature for 2 hours. The agarose plugs are then aspirated, and each well stained with 0.5% crystal violet prepared in 70% methanol. After destaining wells with several washes of water, the viral plaques are then counted.

5.5 Pharmaceutical Compositions and Kits

The present invention encompasses pharmaceutical compositions comprising baicalin and/or its pharmaceutically acceptable derivatives and/or salts. In other embodiments, the treatment method of the present invention further comprises administration of anti-viral agents and/or steroids. In a specific embodiment, the anti-viral agent is an antibody which immunospecifically binds and neutralizes the corona virus or variants thereof, or any proteins derived therefrom. The virus neutralizing antibody neutralizes the infectivity of the virus and protects an animal against disease when wild-type virus is subsequently administered to the animal.

In another specific embodiment, the anti-viral agent is a polypeptide or nucleic acid molecule of the hSARS virus. The pharmaceutical compositions have utility as an anti-viral prophylactic agent and may be administered to a subject where the subject has been exposed or is expected to be exposed to a virus.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu and Wu, 1987, *J. Biol. Chem.* 262:4429 4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In a preferred embodiment, it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non porous, or gelatinous material, including membranes, such as sialastic membranes, or fibers. In one embodiment, administration can be by direct injection at the site (or former site) infected tissues.

In another embodiment, the pharmaceutical composition can be delivered in a vesicle, in particular a liposome (see Langer, 1990, *Science* 249:1527-1533; Treat et al., in *Liposomes in the Therapy of Infectious Disease and Cancer*, Lopez Berestein and Fidler (eds.), Liss, New York, pp. 353-365 (1989); Lopez-Berestein, ibid., pp. 317-327; see generally ibid.).

In yet another embodiment, the pharmaceutical composition can be delivered in a controlled release system. In one embodiment, a pump may be used (see Langer, supra; Sefton, 1987, *CRC Crit. Ref. Biomed. Eng.* 14:201; Buchwald et al., 1980, *Surgery* 88:507; and Saudek et al., 1989, *N. Engl. J. Med.* 321:574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.* 23:61 (1983); see also Levy et al., 1985, *Science* 228:190; During et al., 1989 *Ann. Neurol.* 25:351; Howard et al., 1989 *J. Neurosurg.* 71:105). In yet another embodiment, a controlled release system can be placed in proximity of the composition's target, i.e., the lung, thus requiring only a fraction of the systemic dose (see, e.g., Goodson, *in Medical Applications of Controlled Release, supra, vol.* 2, pp. 115-138 (1984)).

Other controlled release systems are discussed in the review by Langer (*Science* 249:1527-1533 (1990)).

The pharmaceutical compositions of the present invention comprise a therapeutically or prophylactically effective amount of baicalin or pharmaceutically acceptable derivatives or salts thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like.

Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2 ethylamino ethanol, histidine, procaine, etc.

The amount of the pharmaceutical composition of the invention which will be effective in the prevention (i.e., a prophylactically effective amount) and/or treatment (i.e., a therapeutically effective amount) of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 1-15 mg of active compound per kilogram body weight. Suitable dosage ranges for intranasal administration are generally about 0.01 pg/kg body weight to 1 mg/kg body weight. In preferred embodiment, the dose is at least 100, 200, 300, 400, 500, 600, 700, 1000 mg per person per treatment. The course of treatment may be once every 3, 12, 24, 36, 48 hours. The complete treatment cycle may be for 2, 4, 6, 8, 10, 14, 18, 20, 30 days. Effective doses may be extrapolated from dose response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a preferred embodiment, the kit contains an anti-viral agent of the invention, e.g., baicalin and/or its derivatives, alone or in combination with adjuvants, antivirals, antibiotics, analgesic, bronchodilaters, or other pharmaceutically acceptable excipients.

The present invention further encompasses kits comprising a container containing a pharmaceutical composition of the present invention and instructions for use.

5.6 Assays for Detection and Determining Efficacy of Compounds Based on *Scutellaria baicalensis* Georgi Plant Extracts in Therapeutic Methods The efficacy of the treatment methods of the present invention may be evaluated by measuring the levels of the hSARS virus and also other criteria for the clinical diagnosis of the subject. An exemplary method for detecting the presence or absence of a polypeptide or nucleic acid of the invention in a biological sample involves obtaining a biological sample from various sources and contacting the sample with a compound or an agent capable of detecting an epitope or nucleic acid (e.g., mRNA, genomic DNA) of the hSARS virus such that the presence of the hSARS virus is detected in the sample. A preferred agent for detecting hSARS mRNA or genomic RNA of the invention is a labeled nucleic acid probe capable of hybridizing to mRNA or genomic RNA encoding a polypeptide of the invention. The nucleic acid probe can be, for example, a nucleic acid molecule comprising or consisting of the nucleotide sequence of any strains of hSARS virus sufficient to specifically hybridize under stringent conditions to an hSARS mRNA or genomic RNA.

A preferred agent for detecting hSARS virus is an antibody that specifically binds a polypeptide of the invention or any epitope of the hSARS virus, preferably an antibody with a detectable label. Antibodies can be polyclonal, or more preferably, monoclonal. An intact antibody, or a fragment thereof (e.g., Fab or F(ab')2) can be used.

The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The detection method of the invention can be used to detect mRNA, protein (or any epitope), or genomic RNA in a sample in vitro as well as in vivo. For example, in vitro techniques for detection of mRNA include northern hybridizations, in situ hybridizations, RT-PCR, and RNase protection. In vitro techniques for detection of an epitope of the hSARS virus include enzyme linked immunosorbent assays (ELISAs), Western blots, immunoprecipitations and immunofluorescence. In vitro techniques for detection of genomic RNA include northern hybridizations, RT-PCT, and RNase protection. Furthermore, in vivo techniques for detection of hSARS virus include introducing into a subject organism a labeled antibody directed against the polypeptide. For example, the antibody can be labeled with a radioactive marker whose presence and location in the subject organism can be detected by standard imaging techniques, including autoradiography.

In a specific embodiment, the methods further involve obtaining a control sample from a control subject, contacting the control sample with a compound or agent capable of detecting hSARS virus, e.g., a polypeptide of the invention or mRNA or genomic RNA encoding a polypeptide of the invention, such that the presence of hSARS virus or the polypeptide or mRNA or genomic RNA encoding the polypeptide is detected in the sample, and comparing the presence of hSARS virus or the polypeptide or mRNA or genomic RNA encoding the polypeptide in the control sample with the presence of hSARS virus, or the polypeptide or mRNA or genomic DNA encoding the polypeptide in the test sample.

Disease state of SARS may be determined by a kit for detecting the presence of hSARS virus or a polypeptide or nucleic acid of the virus in a test sample. The kit, for example, can comprise a labeled compound or agent capable of detecting hSARS virus or the polypeptide or a nucleic acid molecule encoding the polypeptide in a test sample and a means for determining the amount of the polypeptide or mRNA in the sample (e.g., an antibody which binds the polypeptide or an oligonucleotide probe which binds to DNA or mRNA encoding the polypeptide). Kits can also include instructions for use.

For antibody-based kits, the kit can comprise, for example: (1) a first antibody (e.g., attached to a solid support) which binds to a polypeptide of the invention or an epitope of the hSARS virus; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or to a sequence within the hSARS genome or (2) a pair of primers useful for amplifying a nucleic acid molecule containing an hSARS sequence. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for use.

The assay for determining the efficacy of compounds based on *Scutellaria baicalensis* Georgi plant extracts in therapeutic methods for treating diseases associated with viruses in the order Nidovirales of the family Coronaviridae is based on a determination of whether a baicalin derivative compound has the same binding capability or affinity as baicalin to a target for treatment, prevention, amelioration or management of SARS symptoms. In certain embodiments, the target that the baicalin and/or its derivative binds is a nucleic acid molecule having a nucleotide sequence of, for example, GenBank® accession no. NC_004718, AY304495, AY304494, AY304493, AY304492, AY304491, AY304490, AY304489, AY304488, AY304487, AY304486, AY360146, AY278491, AY310120, AY278489, AY362699, AY362698, AY283798, AY283797, AY283796, AY283795, AY283794, AY268070, AY278741, AY340092, AY351680, AP006561, AP006560, AP006559, AP006558, AP006557, AY278554, AY348314, AY338175, AY338174, AY323977, AY322199, AY322198, AY322197, AH013000, AY322208, AY322207, AY322206, AY322205, AH012999, AY321118, AY323976, AY323975, AY323974, AY286320, AY290752, AY291315, AY307165, AY279354, AY278490, AY278487, AY297028, AY286402, AY274119, AY291451, AY271716, AY282752, AY278488, AY268049, or AY269391, a complement thereof, or a fragment thereof, or protein or polypeptide fragments encoded by such a nucleotide sequence, and/or analogs of such protein/peptides, of the hSARS virus.

In certain embodiments, the baicalin derivatives that are useful in the present method of invention have a similar dissociation constant, total or partial ionic charge or charges.

Many assays may be used to determine the efficacy of a baicalin derivative. An example of such an assay is a binding assay. Such procedures are described in many texts, including but not limited to: Current Protocols in Molecular Biology, John Wiley & Sons, N.Y. (1989), 6.3.1-6.3.6; Basic Methods in Molecular Biology, Elsevier Science Publishing Co., Inc., N.Y. (1986), pp. 75-78, and 84-87; and Molecular Cloning, Cold Spring Harbor Laboratory, N.Y. (1982), pp. 387-389, and are well known to those skilled in the art.

6. EXAMPLES

Ten isolates of hSARS virus isolated from 10 different SARS patients who satisfied the revised WHO criteria of SARS are listed in Table 1.

TABLE 1

| Patient number | Isolate number | Clinical specimen | Sex/ age | Day of specimen after onset of symptoms | RT-PCR result | Day of seroconversion after onset of symptoms | Antibody titer by immuno-fluorescence staining | Hospital |
|---|---|---|---|---|---|---|---|---|
| 1 | M39849* | Lung tissue biopsy | M/54 | 9 | Positive | 9 | 1:160 | KWH |
| 2 | M36871 | NPA | F/41 | 6 | Positive | 12 | 1:1280 | PMH |
| 3 | M65189 | NPA | F/38 | 4 | Positive | 18 | 1:640 | PYNEH |
| 4 | M67349 | NPA | F/41 | 6 | Positive | 20 | 1:640 | PYNEH |
| 5 | M70221 | NPA | M/30 | 10 | Positive | 22 | 1:2560 | PYNEH |
| 6 | M71749 | NPA | M/48 | 11 | Positive | 24 | 1:160 | PYNEH |
| 7 | M51776 | NPA | F/39 | 6 | Positive | 10 | 1:640 | TKOH |
| 8 | M61558 | NPA | F/53 | 10 | Positive | 18 | 1:40 | UCH |
| 9 | M61576 | Urine | M/40 | 12 | Positive | 18 | 1:40 | UCH |
| 10 | M61565 | NPA | M/28 | 10 | Positive | 18 | 1:40 | UCH |

Note.
KWH, Kwong Wah Hospital;
NPA, Nasopharyngeal aspirates;
PMH, Princess Margaret Hospital;
PYNEH, Pamela Youde Nethersole Eastern Hospital;
TKOH, Tseung Kwan O Hospital;
UCH, United Christian Hospital;
*Prototype virus.

The State Administration of Traditional Chinese Medicine of People's Republic of China recently formed a panel of Chinese Medicine specialists to draw up a "Technical Scheme (Tentative) for the Prevention and Treatment of Severe Acute Respiratory Syndrome (SARS) Using Traditional Chinese Medicine." In the Scheme, a recipe "Qing Fei Jie Du Tang" (soup for clearing the lung and detoxification) was recommended which consisted of Huang Qi (*Astragalus membranaceus*) 15 gm, Chai Hu (*Bupleurum chinense*) 10 gm, Ma Huang (*Ephedra sinica*) 5 gm, Xing Ren (*Prunus armeniaca*) 10 gm, Sheng She Gao (Plaster Stone) 30 gm, Sheng Yi Ren (*Coix lacryma-jobi*) 15 gm, Gua Wei Pi (*Benincasa hispida*) 15 gm, Jie Geng (*Platycodon grandiflorum*) 9 gm, Bo He (*Mentha haplocalyx*) 6 gm, Huang Qin (*Scutellaria baicalensis*) 10 gm, Sheng Gan Cao (*Glycyrrhiza uralensis*) 5 gm, Jin Yin Hua (*Flos lonicerae*) 15 gm, and Qing Hao (*Artemisia apiacea*) 15 gm.

The chemical structure and pharmacological properties of baicalin are shown in FIG. 1 and Table 2, respectively. Baicalin was extracted as we previously reported [Lu H T et al., "Application of high-speed counter-current chromatography to the preparative separation and purification of baicalin from the Chinese medicinal plant *Scutellaria baicalensis*." *J Chromatogr A* 2003; 1017:117-123]. Briefly, in the case of the roots of *Scutellaria baicalensis* Georgi, it was dehydrated to a constant weight at 60° C. and then pulverized. Thirty gm of the pulverized sample was put into a 1000-ml flask with 400 ml of methanol-water (70:30, v/v). After extraction at ambient temperature under sonication for 30 min, the mixture was filtered. The extraction procedure was repeated twice (200 ml each time). The filtrates were combined and evaporated to dryness by rotary evaporation. Crude baicalin (16.9 g) was yielded and stored in a refrigerator for the subsequent high-speed counter-current chromatographic separation with a two-phase solvent system composed of n-butanol-water (1:1, v/v). In each separation, the multilayer-coiled column was first filled entirely with the upper nonaqueous stationary phase. Then 200 mg of the sample dissolved in 5 ml of both phases was loaded. The mixture was centrifuged at 900 rpm while the lower aqueous mobile phase was pumped into the head end of the inlet column at a flow-rate of 1.0 ml/min by an HPLC pump.

TABLE 2

| Compounds | Baicalin |
|---|---|
| Name of herbs | *Scutellaria baicalensis* (Huang Qin) |
| Chemical structure | Please refer to FIG. 1 |
| Chemical formula | $C_{21}H_{18}O_{11}$ |
| Molecular weight | 446.38 |
| Thermal stability | Stable at boiling temperature (a typical extraction method) [Han RJ et al., "Research on the extraction and separation technology." Journal of Agricultural Engineering 2000; 16: 118-122) (in Chinese)] |
| Serum level (after oral administration) | $C_{max}$ = 60 ng/mL (189.8 mg/person, in human). The amount (i.e., 189.8 mg/person) used for the experiment is very low [Muto R et al., "The chemical structure of new substance as the metabolite of baicalin and time profiles for the plasma concentration after oral administration of Sho-Saiko-To in human." Yakugaku Zasshi 1998; 118: 79-87 (in Japanese)]. |
| Standard doses in | ~1500 mg baicalin (as tablets) [Zui YC, Modern Pharmacy (People's Army |

TABLE 2-continued

| Compounds | Baicalin |
|---|---|
| oral administration in humans | Medicinal Press (1999)]; also can be up to ~6000 mg baicalin (calculated from herb, assuming 30 g herb used; the herb may contain up to 20% as baicalin). |
| Serum level (after intravenous administration) | $C_{max}$ = 74 µg/mL (360 mg/person) [Wu CL et al., "Effects of Yan Shuan Ji Mei Su on the pharmacokinetics of Shuang Huang Liang injection preparations." Acta Chinese Medicine and Pharmacology 1998; 3: 46-47 (in Chinese); Hua QG et al., "Studies on quality standards of Shuang Huang Liang injection preparation." Prepared Chinese Medicines 1996; 18: 13-15 (in Chinese)] |
| Standard doses in intravenous administration in humans | ~600 mg baicalin [Zui YC, Modern Pharmacy (People's Army Medicinal Press (1999)] |
| Half life (in humans) | ~3 hrs in humans Muto R et al., "The chemical structure of new substance as the metabolite of baicalin and time profiles for the plasma concentration after oral administration of Sho-Saiko-To in human." Yakugaku Zasshi 1998; 118: 79-87 (in Japanese)]. |
| Antiviral effect | Inhibition of HIV-1 [Kitamura K et al., "Baicalin: an inhibitor of HIV-1 production in vitro." Antiviral Res 1998; 37: 131-40 |

After the mobile phase front emerged and hydrodynamic equilibrium was established in the column, as indicated by a clear mobile phase eluting at the tail outlet, the sample solution was injected through the injection valve. The effluent from the outlet of the column was continuously monitored with a UV-Vis detector at 277 nm and the chromatogram was recorded by an L 120 E flat-bed recorder. Peak fractions were collected and purity checked according to the elution profile as determined by HPLC as shown in FIGS. 3 and 4 [Also see Lu H T et al., "Application of high-speed counter-current chromatography to the preparative separation and purification of baicalin from the Chinese medicinal plant *Scutellaria baicalensis.*" *J Chromatogr A* 2003; 1017:117-123]. The concentration of baicalin in the cell culture system was monitored by HPLC [Lu H T et al., 2003].

The procedures used for in-vitro antiviral susceptibility testing are as follows. The in-vitro susceptibility against the prototype hSARS virus was performed in 96-well microtitre plates seeded with foetal rhesus kidney-4 cells. Two-fold dilutions of antiviral agents starting from more than 4 times the peak serum concentration after the maximum therapeutic dose to less than one-quarter of the trough serum concentration were tested in quadruplicate against 100 TCID50 of hSARS virus. A corresponding set of cell controls with drug but without virus inoculation was used as controls for drug toxicity. The cells were scored for the inhibition of the cytopathic effect (CPE) at 48 hours and at 72 hours. Their antiviral activities were also compared in both fRHK-4 and Vero-E6 cell lines. Those likely to have clinically significant inhibitory activity were tested by the plaque reduction assay.

For the plaque reduction assay, a 24-well tissue culture plates with a confluent cell monolayer ($1 \times 10^5$ cells per well) in 1.0 ml of minimal essential medium (MEM) with 10% fetal calf serum (FCS) were prepared. After the medium was aspirated, 50-100 plaque forming units (PFU) of SARS associated coronavirus (in 1% FCS/MEM containing antivirals at appropriate concentrations) was added to each well. Plates were incubated for 2 hours at 37° C. in 5% $CO_2$. The inoculum was aspirated and 1.0 ml of overlay (1.0% low-melting point agarose in 1% FCS/MEM with corresponding drug dilutions) was added to each well. Plates were further incubated for 48 hours at 37° C. in 5% $CO_2$. Cells were fixed by adding 2 ml of 10% formaldehyde and the plates were incubated at room temperature for 2 hours. The agarose plugs were aspirated and each well was stained with 0.5% crystal violet prepared in 70% methanol. After destaining wells with several washes of water, the viral plaques were counted.

Figure 1:
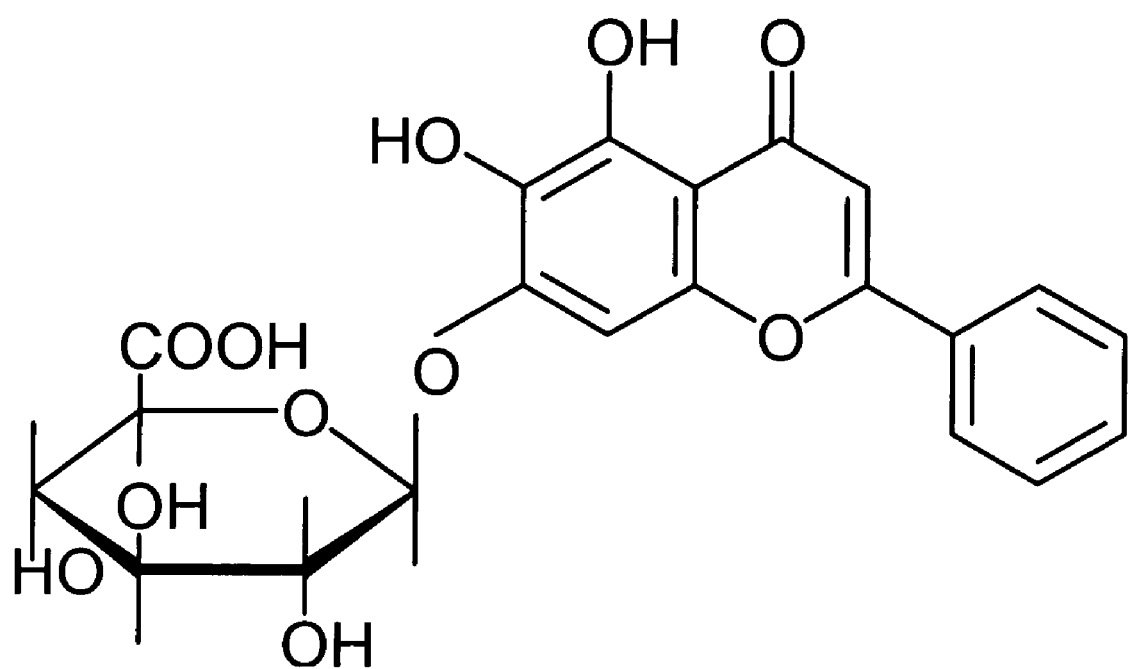
FIG. 1 shows the chemical structure of Baicalin.
Figure 2:
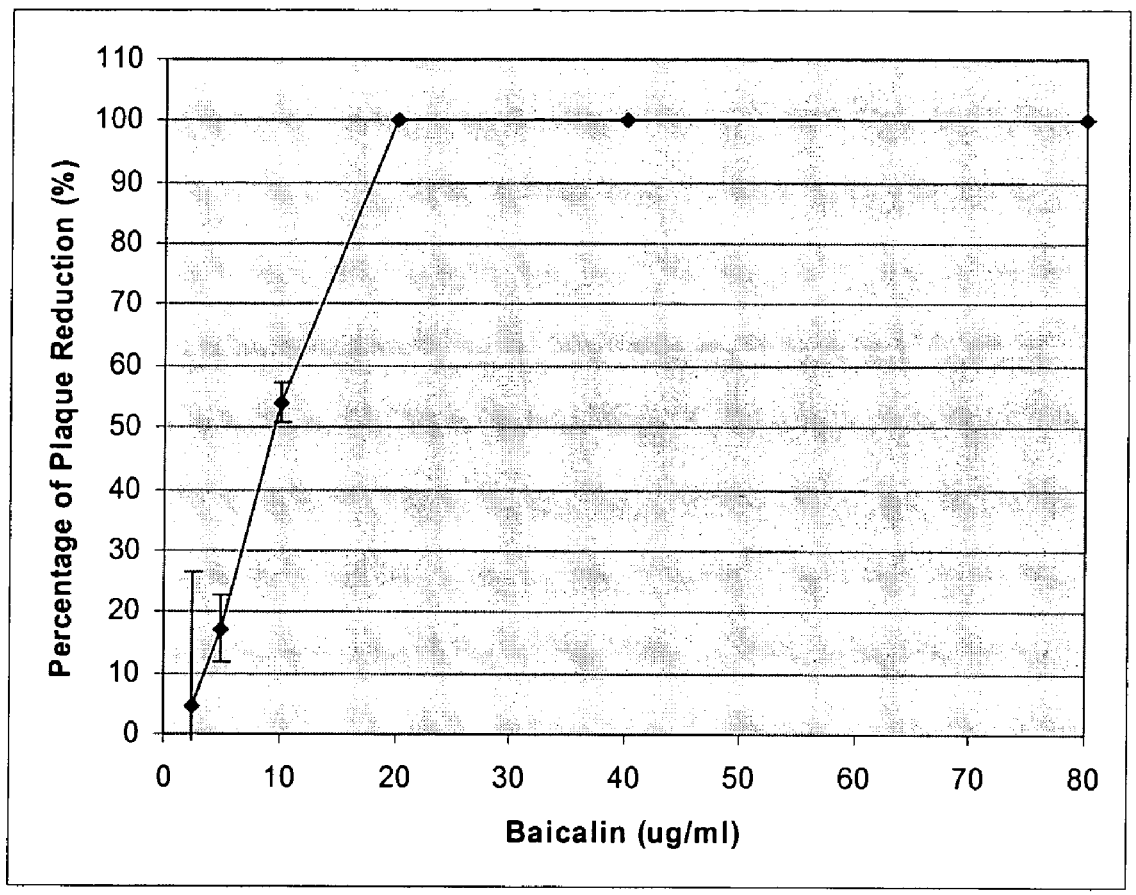
FIG. 2 shows the results of an in vitro Plaque reduction assay using selected compounds with antiviral activities. Results were expressed as percentage plaque reduction, where the percentage reduction of the number of Plaque Forming Unit (PFU) from positive controls (no drugs added) was taken as 0%.

The effective concentration of baicalin in fRhK-4 cell line by neutralization test is around 12.5 to 25 µg/ml at 48 hours and 25 to 50 µg/ml at 72 hours (Table 3). Similar results are found with plaque reduction assay (FIG. 2).

TABLE 3

Antiviral activity of baicalin against 10 strains of SARS-CoV measured by neutralization test using fRhK4 cell line

| Compound | $EC_{50}$ (µg/ml) at 48 hrs | $EC_{50}$ (µg/ml) at 72 hrs | $CC_{50}$ (µg/ml) | SI = $CC_{50}$/ $EC_{50}$ at 48 hrs |
|---|---|---|---|---|
| Baicalin | 12.5-25 | 25-50 | >100 | >8 |

Note.
$EC_{50}$, effective concentration of compound required to inhibit the cytopathic effect to 50% of control value;
$CC_{50}$, cytotoxic concentration of compound that reduced cell viability to 50%;
SI, selectivity index.

7. EQUIVALENTS

Those skilled in the art will recognize, or be able to ascertain many equivalents to the specific embodiments of the invention described herein using no more than routine experimentation. Such equivalents are intended to be encompassed by the following claims.

All publications, patents and patent applications mentioned in this specification are incorporated herein by reference in their entireties into the specification to the same extent as if each individual publication, patent or patent application was specifically and individually indicated to be incorporated herein by reference in its entirety.

Citation or discussion of a reference herein shall not be construed as an admission that such is prior art to the present invention.

What is claimed is:

1. A method for treating a subject infected with a SARS virus, said method comprising administering to a subject in need thereof a therapeutically effective amount of a pharmaceutical composition comprising a compound having the following formula:

wherein each of $X_1$, $X_2$, $X_3$, $X_4$, $X_5$, $X_a$, $X_b$, $X_c$, $X_d$, $X_e$ and $X_f$ is independently O or S;

each of $Y_1$, $Y_2$, $Y_3$, $Y_4$ and $Y_6$ is independently H or $CH_3$;

each of $R_4$, $R_5$, $R_a$, $R_b$ and $R_c$ is independently H, $(C_1-C_{10})$ alkyl optionally substituted with 1-5 $R_y$ groups, or $(C_1-C_{10})$alkyl-O—$(C_1-C_{10})$alkyl, each $(C_1-C_{10})$alkyl of which is optionally substituted with 1-5 $R_y$ groups;

each $R_y$ is independently $R_q$ or —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, $(C_8-C_{14})$bicycloalkenyl, —$(C_8-C_{14})$tricycloalkenyl, -phenyl, -naphthyl or —$(C_{14})$aryl, each of which is unsubstituted or substituted with one or more $R_z$ groups;

each of $R_1$, $R_2$ and $R_3$ is independently $R_q$ or $(C_1-C_{10})$alkyl, —$(C_2-C_{10})$alkenyl, —$(C_2-C_{10})$alkenyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, $(C_8-C_{14})$bicycloalkenyl, —$(C_8-C_{14})$tricycloalkenyl, -phenyl, -naphthyl or —$(C_{14})$aryl, each of which is unsubstituted, substituted with one or more $R_q$ groups, substituted with one or more $R_z$ groups, or substituted with one or more $R_q$ groups and one or more groups;

$R_f$ is H, $(C_1-C_{12})$alkyl optionally substituted with 1-5 $R_y$ groups, $(C_1-C_{12})$alkyl-O—$(C_1-C_{12})$alkyl, each $(C_1-C_{12})$alkyl of which is optionally substituted with 1-5 $R_y$, or a counterion;

each $R_q$ is independently CN, OH, halo, $N_3$, $NO_2$, $N(R_z)_2$=$NR_z$, CH=$NR_z$, $NR_zOH$, $OR_z$, $COR_z$, $C(O)OR_z$, $OC(O)R_z$, $OC(O)R_z$, $OC(O)OR_z$, $SR_z$, $S(O)R_z$ or $S(O)2R_z$;

each $R_z$ is independently —$(C_1-C_6)$alkyl, —$(C_2-C_6)$alkenyl, $(C_2-C_6)$alkenyl, $(C_3-C_8)$cycloalkyl, —$(C_5-C_8)$ cycloalkenyl, -phenyl, -(3- to 5-membered)heterocycle, $C(halo)_3$ or $CH(halo)_2$; and n is 0, 1, 2, 3, 4, or 5 and/or a pharmaceutically acceptable salt thereof, together with a pharmaceutically acceptable carrier and/or excipient, wherein said compound is at least 95% pure.

2. The method of claim 1, wherein the virus is a hSARS virus.

3. The method of claim 1, wherein the subject is a mammal.

4. The method of claim 3, wherein the subject is a human.

5. The method of claim 1, wherein the method further comprises administering a therapeutically effective amount of steroid, antiviral agent, an antibiotic, an analgesic, and/or a bronchodilator.

6. A method of treating a subject infected with hSARS virus, said method comprising administering to the subject a therapeutically effective amount of a pharmaceutical composition comprising a compound having the following formula:

and a pharmaceutically acceptable carrier, wherein said compound is at least 95% pure.

7. The method of claim 6, wherein the composition further comprises a therapeutically effective amount of a steroid, an antiviral agent, an antibiotic, an analgesic, and/or a bronchodilator.

8. The method, according to claim 1, wherein said compound is at least 95% pure.

9. The method, according to claim 1, wherein the compound is at least 99% pure.

10. The method, according to claim 6, wherein the compound is at least 99% pure.

* * * * *

UNITED STATES PATENT AND TRADEMARK OFFICE
CERTIFICATE OF CORRECTION

PATENT NO. : 7,605,135 B2  
APPLICATION NO. : 10/983985  
DATED : October 20, 2009  
INVENTOR(S) : Kwok-Yung Yuen et al.

Page 1 of 1

It is certified that error appears in the above-identified patent and that said Letters Patent is hereby corrected as shown below:

Column 1,  
Line 39 "a typical" should read --atypical--.  
Lines 45 and 46 "a typical" should read --atypical--.  
Line 52 "a typical" should read --atypical--.

Column 25,  
Line 31 "or $(C_1-C_{10})$" should read --or $–(C_1-C_{10})$--.  
Line 40 "one or more groups;" should read --one or more $R_z$ groups:--.

Column 26,  
Line 4 claim 1 "or $CH(halo)_2$; and" should read --or $–CH(halo)_2$; and--.

Signed and Sealed this

Eighth Day of December, 2009

David J. Kappos  
*Director of the United States Patent and Trademark Office*

UNITED STATES PATENT AND TRADEMARK OFFICE
CERTIFICATE OF CORRECTION

PATENT NO. : 7,605,135 B2 Page 1 of 1
APPLICATION NO. : 10/983985
DATED : October 20, 2009
INVENTOR(S) : Yuen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1353 days.

Signed and Sealed this

Fifth Day of October, 2010

David J. Kappos
*Director of the United States Patent and Trademark Office*